US00RE35724E

United States Patent [19]

Pasquale

[11] E Patent Number: Re. 35,724

[45] Reissued Date of Patent: Feb. 3, 1998

[54] CONTRACEPTION SYSTEM AND METHOD

[75] Inventor: Samuel A. Pasquale, Basking Ridge, N.J.

[73] Assignee: Bio-Technology General Corp., Iselin, N.J.

[21] Appl. No.: 369,309

[22] Filed: Jan. 6, 1995

Related U.S. Patent Documents

Reissue of:

[64] Patent No.: 4,921,843
Issued: May 1, 1990
Appl. No.: 260,447
Filed: Oct. 20, 1988

U.S. Applications:

[63] Continuation of Ser. No. 875,277, Apr. 28, 1982, abandoned.

[51] Int. Cl.[6] ..... A61K 31/56

[52] U.S. Cl. ..... 514/170; 514/843

[58] Field of Search ..... 514/170, 843

[56] References Cited

U.S. PATENT DOCUMENTS

| | | | |
|---|---|---|---|
| 3,409,721 | 11/1968 | Applezweig | 424/239 |
| 3,502,772 | 3/1970 | Ijzerman | 424/239 |
| 4,372,951 | 2/1983 | Vorys | 514/170 |
| 4,544,554 | 10/1985 | Pasquale | 514/170 |
| 4,616,006 | 10/1986 | Pasquale | 514/170 |
| 4,621,079 | 11/1986 | Lachnit-Fixson et al. | 514/170 |
| 4,628,051 | 12/1986 | Pasquale | 514/170 |

FOREIGN PATENT DOCUMENTS 28769 10/1967 Australia .

OTHER PUBLICATIONS

Goodman and Gilman, "The Pharmacological Basis of Therapeutics", 7th ed. (1985), pp. 1430–1436.

Rote Liste, 1982, Abstract No. 75157.

*Primary Examiner*—Kimberly Jordan
*Attorney, Agent, or Firm*—John P. White

[57] ABSTRACT

A method of contraception is disclosed which comprises a two-stage protocol. In the first stage, an estrogenic compound in a first composition is administered daily as the sole contraceptively active substance to a human female from about Day 2 to about Day 7 of her menstrual cycle, where Day 1 is the first day of menses. The second stage of the protocol occurs immediately thereafter during which at least one follow-up composition containing a progestin is administered daily to the same human female. The follow-up composition can contain a progestin as the sole contraceptively active ingredient, or can contain a combination of an estrogenic compound with a progestin in different weight ratios. A drug delivery system containing daily dosage units is also described.

28 Claims, No Drawings

CONTRACEPTION SYSTEM AND METHOD

Matter enclosed in heavy brackets [ ] appears in the original patent but forms no part of this reissue specification; matter printed in italics indicates the additions made by reissue.

*This is a continuation of application Ser. No. 07/875,277, filed Apr. 28, 1992.*

TECHNICAL FIELD

This invention relates to the practice of contraception utilizing a two-stage protocol that minimizes this incidence of breakthrough bleeding.

Background of the Invention

Oral contraceptives first became available in the early 1960's. Through continued research, new lower-dose estrogen products of high effectiveness have been developed. The oral administration of combination-type preparations containing estrogens and progestins has been known for some time. The administration of purely sequential preparations to mimic the normal 28-day menstrual cycle of the patient is also known. In such instances, an estrogen is administered at a high dosage, in the absence of a progestin, over a period of fourteen to sixteen days, thereafter the estrogen is administered at the same high dosage in combination with a relatively high amount of progestin over a period of five to six days, and during the next seven to eight days there is no administration of estrogen or progestin. Physician's Desk Reference, 30th edition, pages 1026, 1127 and 1532, respectively (1976).

It has more recently been published in Goodman and Gilman, The Pharmacological Basis of Therapeutics, 7th edition, pages 1430–1436 (1985), that sequential combination administration includes the usage of an estrogen at a high dosage, in the absence of a progestin, over a period of seven days, thereafter the estrogen is administered at the same high dosage in combination with a relatively high amount of s progestin over a period of 15 days, and during the next six days there is no administration of estrogen or progestin.

In Vorys U.S. Pat. Nos. 4,292,315 and 4,372,951, various sequential and combination oral contraceptive delivery systems are disclosed. All of the systems described in the patents to Vorys comprise an early 7-day period in which no exogenous steroids are administered, followed by a 7-day period in which a pharmacologically low dose of an unopposed estrogen or progestin steroid is administered daily, followed by an arbitrary 14-day period in which various combinations of estrogen and progestin are administered daily in various pharmacological dosages. None of the systems described in Vorys utilize the administration of an unopposed estrogen during the initial seven days of the menstrual cycle.

Biphasic and triphasic oral contraceptive combinations have been described in Pasquale U.S. Pat. Nos. 4,530,839; 4,544,554; and 4,628,051. The described biphasic and triphasic oral contraceptive systems do not include the administration of an unopposed estrogenic compound during the first seven days of the menstrual cycle. In the biphasic combination type oral contraceptives, a combination of an estrogen and a low dosage of a progestin is first administered for 10–12 days, Subsequently, a combination of the same dosage of estrogen and an increased progestin dosage is administered for the remaining 9–11 days of a 21-day regimen. The biphasic systems were developed in an effort to reduce dosage and keep bleeding patterns at an acceptable level.

In the triphasic oral contraceptive regimen, an estrogen dosage is kept constant throughout the 21-day regimen while the progestin dosage is gradually increased is successive steps. Thus, the 21-day regimen comprises an initial 7-day period in which a daily dose of a combination of an estrogenic compound together with a low dosage of a progestin is administered; followed by a 7-day period in which a daily dosage of an estrogenic compound together with a moderate progestin dosage is administered; followed by a terminal 7-day period in which a daily dosage of an estrogenically effective compound together with a high dose of an progestin is administered to a human female. This regimen is then followed by a 7-day period in which no hormone is given.

A disadvantage of the above-described oral contraceptive systems is that there often occurs an incidence of breakthrough bleeding and spotting. Additionally, there is a risk of escaped ovulation or pregnancy, especially if a daily tablet is missed during the cycle. Chowdhury et al., Contraception, 22:241–247 (1980); Molloy et al., Brit. Med. J. 290:1474–1473 (1985).

SUMMARY OF THE INVENTION

The present invention relates to a two-stage oral contraceptive system in which an unopposed estrogenic compound is administered during a terminal portion of the first 7-day segment of the menstrual cycle, counting as Day 1 the onset of menses. In the contemplated method aspect, an initial composition containing an estrogenic compound as the sole contraceptively active ingredient is administered during the terminal portion of the first 7-day segment of the menstrual cycle, preferably from about Day 2 to about Day 7, inclusive, of the menstrual cycle, at a daily dosage equivalent in estrogenic activity to about 0.01 to about 0.04 mg of 17-alpha-ethinyl estradiol, to a human female of child-bearing age for contraception purposes. Following this initial administration of a relatively small dosage of an unopposed estrogenic compound, the second stage of the contemplated contraceptive system is commenced. In the second stage, a daily administration of a follow-up composition containing a progestin, alone or in combination with an estrogenic compound, is continued to about Day 28 of the menstrual cycle.

The method of contraception of the present invention contemplates that the follow-up composition, administered during Days 7 to 28 of the menstrual cycle preferably contains a combination of an estrogenic compound and a progestin. The composition administered during the second stage can be a uniphasic, biphasic or triphasic combination oral contraceptive system.

In the present drug delivery system at least 24 separate dosage units are included for successive daily oral administration. Preferably, at least three initial dosage units contain a pharmacologically active daily dosage amount of an unopposed estrogenic compound, and the remainder each contain a pharmacologically active daily dosage amount of a composition containing a progestin as aforesaid.

DETAILED DESCRIPTION OF PREFERRED EMBODIMENTS

The present invention provides a two-stage protocol which is utilized as a method of contraception in a human Female while minimizing the incidence of breakthrough bleeding. In the first stage of this protocol, a composition containing an estrogenic compound as the sole contraceptively active ingredient is administered during a terminal portion of the first 7-day segment of the menstrual cycle, preferably from Day 4 to Day 7 of the menstrual cycle. In the second stage of the protocol commencing immediately after the first stage, a follow-up daily dosage of a composition containing a progestin is administered through Day 28 of the menstrual cycle. Throughout the present specification and claims, Day 1 of the menstrual cycle is defined as the day on which onset of menses is noted.

This follow-up progestin-containing composition can be:

(1) a composition containing an unopposed progestin;

(2) a combination of an estrogenic compound and a progestin;

(3) a biphasic oral contraceptive in which one dosage of a combination of an estrogenic compound and a progestin is administered daily for about 10 days of the menstrual cycle, and followed by administration of a follow-up dosage of an estrogenic compound and a progestin, which is administered daily for the remainder of the menstrual cycle; or (4) a triphasic oral contraceptive, in which three group of seven daily dosages each, are administered consecutively in a predetermined sequence. The dosage units in each such group contain a composition of an estrogenic compound and a progestin; however all three groups do not contain the same weight ratio of estrogenic compound and progestin.

Estrogenic compounds, as the term is used herein, includes hormones as well as other compounds that exhibit estrogenic activity. That is, an estrogenic compound is a compound having the ability to elicit a physiological response similar to that normally produced by endogenous estrogen in a human female, such as inhibition of follicle stimulating hormone (FSH) secretion. Illustrative such compounds include 17-alpha-ethinyl estradiol 3-methylether, mestranol, 17-beta-estradiol, 17-alpha-ethinyl estradiol, and the like.

Progestins utilizable in the present invention include progestrone and its derivatives such as, for example, 17-hydroxy progestrone esters and 19-nor-17-hydroxy progestrone esters, 17-alpha-ethinyl testosterone, 17-alpha-ethinyl-19-nortestosterone and derivatives thereof, norethindrone, norgestrel, norgestamate. Desorgestrel, and D-17-beta-acetoxy-17-beta-ethyl17-alpha-ethinyl-gon-4-en-3-one oxime. The preferred progestins are norethindrone, D-norgestrel and D-17-beta-acetoxy-13-beta-ethyl-17-alpha-ethinyl-gon-4-en-3-one oxime.

A preferred dosage of an estrogenic compound in the present invention is a dosage that is equivalent in estrogenic activity to about 0.01 to about 0.04 milligrams (mg) of 17-alpha-ethinyl estradiol.

Preferred dosages for the progestin of the present invention are about 0.5 to about 1.0 mg.

In spontaneous menstrual cycles, the dominant follicle is recruited during the first six days of the menstrual cycle, where Day 1 is counted as the first day of bleeding. During this period of time, the FSH level is slightly elevated, and then decreases to peak again at mid-cycle at the time of ovulation. The present invention utilizes the fact that estrogen suppresses FSH levels. Thus, by administration of estrogen during the first seven days of the menstrual cycle, the follicular period, escape ovulation is less likely to occur if a dosage unit is missed.

Estrogen administration at this early stage of the menstrual cycle also prevents recruitment of the dominant follicle and thus allows a reduction in the dose of the estrogen and progestin in the combination oral contraceptive needed between Days 7 and 28 of the menstrual cycle to prevent conception. Additionally, estrogens stimulate progesterone receptor sites. By simulation of progesterone receptors early in the menstrual cycle, estrogen administration allows a reduction in the incidence of intermenstrual bleeding. That is, breakthrough bleeding and spotting are minimized with the low-dose oral contraceptives of the present invention.

Following the period of unopposed estrogen administration during the follicular period of the menstrual cycle, a second stage of administration comprising a 21-day regime of daily dosages of a standard oral contraceptive composition is followed. This second stage period comprises the administration of successive daily dosages of a progestin-containing composition.

Illustrative of the second stage of the method of the present invention are oral contraceptive compositions which contain one or more combination dosages of an estrogenic compound and a progestin, or a progestin alone. Such following-up combinations of an estrogenic compound and a progestin can constitute a uniphasic, biphasic or triphasic oral contraceptive system.

In the uniphasic system, a single dosage of a combination of an estrogenic compound and a progestin is administered daily for the 21 days of the second stage of the method of the present invention. In a preferred uniphasic system, a daily dosage unit containing 0.035 mg ethinyl estradiol and 0.5 mg norethindrone is administered.

In the biphasic system, two different dosage levels of an estrogenic compound and a progestin are administered, one level for about 7 to about 10 days of the 21-day regimen and the second dosage level for the remainder of the menstrual cycle.

In one preferred system, plural follow-up compositions are administered in sequence. The daily dosage of the estrogenic compound is substantially the same in all administered follow-up compositions, and the daily dosage of the progestin is greater in each successive follow-up composition. In a particularly preferred embodiment, a daily dosage of 0.035 mg ethinyl estradiol and 0.5 mg of norethindrone is administered to a female for about 7 to about 10 days, followed immediately in sequence by a daily dosage of 0.035 mg ethinyl estradiol and 1.0 mg norethindrone for the remainder of the menstrual cycle.

In the triphasic system, administration is divided into three approximately 7-day periods of daily oral contraceptive administration; the daily dosage level of the combination of an estrogenic compound and a progestin varies between successive approximately 7-day regimen periods. In the triphasic system, the three respective dosages can be different from each other or can be similar to each other during the first and third 7-day periods of administration.

In a particularly preferred embodiments, a daily dosage of 0.035 mg ethinyl estradiol and 0.5 mg norethindrone is administered to a female for about seven days, followed immediately in sequence by the daily administration of 0.035 mg ethinyl estradiol and 0.75 mg norethindrone for the next seven days, and then followed immediately in sequence by the daily administration of 0.035 mg ethinyl estradiol and 1.0 mg norethindrone for the remaining seven days of the menstrual cycle.

In a second preferred system of contraception, plural follow-up compositions are administered in sequence in which the daily dosage of the estrogenic compound is substantially the same in all administered follow-up compositions and in which the daily dosage of progestin in successive follow-up compositions first increases to a value greater than the level of progestin first administered and then decreases to a level corresponding to the same value as that of the progestin first administered as the daily progestin dosage. In a particularly preferred embodiment, a daily dosage of 0.035 mg ethinyl estradiol and 0.5 mg norethindrone is administered for about seven days, immediately followed by a daily administration of a dosage of 0.035 mg ethinyl estradiol and 1.0 mg norethindrone for about the next seven days, and then immediately followed by a daily administration of a dosage of 0.035 mg ethinyl estradiol and 0.5 mg norethindrone for the remaining seven days of the menstrual cycle.

The estrogen and progestin components in the second stage of the present invention are preferably administered admixed together, but they can also be administered separately. In general, the effective agents are compounded together to form a single dosage unit. Preferred dosage units are tablets or pills.

In the dosage units, the effective contraceptive agents are combined with the excipients, vehicles, and pharmacologically acceptable carriers commonly employed by one of ordinary skill in the preparation of pharmaceuticals in accordance with generally accepted pharmaceutical practices. Exemplary pharmaceutically acceptable carriers include corn starch, lactose, dicalcium phosphate, thickeners such as tragacanth and methylcellulose U. S. P., Freely divided $SiO_2$, polyvinylpyrrolidone, magnesium stearate and the like. Additionally, a solid carrier can include biodegradable and non-biodegradable polymers and polypeptide carriers. Antioxidants, such as methylparaben and propylparaben can be present, as can sweeteners such as cane or beet sugar, sodium saccharin, sodium cyclamate and the dipeptide methylester sweeteners commercially available under the trademark NUTRA SWEET (aspartame) by the Nutrasweet Company (North Chicago, Ill.). Among the various oral dosage forms, tablets, capsules, and pills are particularly preferred.

A drug delivery system embodying the present invention contains a pharmaceutical package having at least 24 active dosage units arranged sequentially therein. Preferably, the pharmaceutical package contains 28 dosage units, including placebo units. This drug delivery system has at least four dosage units for the first stage of the method of the present invention and 21 dosage units for the second stage thereof. A single dosage unit is a daily dosage unit to be taken each day over the period of administration.

In a particularly preferred embodiment, the drug delivery system of the present invention contains 28 tablets. The first set of tablets in each sequence contains a placebo, the next four or five tablets in the sequence contain a composition of an unopposed estrogenic compound, and the remaining 21 tablets in the sequence contain a desired follow-up oral contraceptive composition as described hereinabove.

In a preferred embodiment the twenty one follow-up dosage units each contain substantially the same daily dosage of an estrogenic compound and a progestin.

In an alternate preferred embodiment the twenty one follow-up dosage units comprise a first group of 10 dosage units that each contain a first contraceptively effective daily dosage of an estrogenic compound and a progestin, and a second group of 11 dosage units that each contain a second follow-up contraceptively effective dosage of a progestin and an estrogenic compound.

In another alternate preferred embodiment, the twenty-one follow-up dosage units comprise three consecutive groups of about seven dosage units each, where each group contains contraceptively effective daily dosage units of an estrogenic compound and a progestin. The estrogenic compound and progestin in each individual group are present in substantially the same weight ratio, with the proviso that the weight ratios of the estrogenic compound to the progestin are different for the respective dosage units that constitute consecutively administered groups.

Certain specific examples are provided hereinbelow for purposes of illustration only and are not to be taken as limiting.

EXAMPLE 1

Estrongenic Compound Plus Uniphasic Contraceptive Regimen

A placebo tablet is administered to a menstruating human female for the first two days of the menstrual cycle, at Day 1 is the first day of bleeding. On Days 3 to 7, inclusive, 0.02 mg of ethinyl estradiol is administered daily. From Day 8 to the end of the menstrual cycle at Day 28, inclusive, a daily dosage of 0.035 mg of ethinyl estradiol together with 0.5 mg of norethindrone is administered. This regimen is illustrated in TABLE I.

TABLE I

| Contraceptive Regimen | | | | | | | |
|---|---|---|---|---|---|---|---|
| Day | 1 | 2 | 3 | 4 | 5 | 6 | 7 |
| Composition | P | P | E | E | E | E | E |
| Day | 8 | 9 | 10 | 11 | 12 | 13 | 14 |
| Composition | C | C | C | C | C | C | C |
| Day | 15 | 16 | 17 | 18 | 19 | 20 | 21 |
| Composition | C | C | C | C | C | C | C |
| Day | 22 | 23 | 24 | 25 | 26 | 27 | 28 |
| Composition | C | C | C | C | C | C | C |

Day = Day of the Menstrual Cycle: Day 1 as the first day of bleeding.
Composition = the active ingredient(s) present in a daily dosage unit taken on the respective day of the menstrual cycle.
P = placebo, contains no contraceptively active ingredients.
E = 0.02 mg ethinyl estradiol.
C = combination containing 0.035 mg ethinyl estradiol and 0.5 mg norethindrone.

EXAMPLE 2

Estrogenic Compound Plus Uniphasic Contraceptive Regimen

A placebo tablet is administered to a menstruating human female for the first two days of menstrual cycle, where Day 1 is the first day of bleeding. On Days 3 to 7, inclusive, 0.04 mg of ethinyl estradiol is administered daily. From Day 8 to the end of her menstrual cycle at Day 28, inclusive, a daily dosage of 0.035 mg ethinyl estradiol together with 0.5 mg norethindrone is administered. This regimen is illustrated in TABLE II.

TABLE II

| Contraceptive Regimen | | | | | | | |
|---|---|---|---|---|---|---|---|
| Day | 1 | 2 | 3 | 4 | 5 | 6 | 7 |
| Composition | P | P | E | E | E | E | E |
| Day | 8 | 9 | 10 | 11 | 12 | 13 | 14 |
| Composition | C | C | C | C | C | C | C |
| Day | 15 | 16 | 17 | 18 | 19 | 20 | 21 |
| Composition | C | C | C | C | C | C | C |
| Day | 22 | 23 | 24 | 25 | 26 | 27 | 28 |
| Composition | C | C | C | C | C | C | C |

Day = Day of the Menstrual Cycle: Day 1 is the first day of bleeding.
Composition = the active ingredient(s) present in a daily dosage unit taken on the respective day of the menstrual cycle.
P = placebo, contains no contraceptively active ingredient.
E = 0.04 mg ethinyl estradiol.
C = combination containing 0.035 mg ethinyl estradiol and 0.5 mg norethindrone.

EXAMPLE 3

Estrogenic Compound Plus Triphasic Contraceptive Regimen

A placebo dosage is administered to a menstruating human female for the first two days of her menstrual cycle, where Day 1 is the first day of bleeding. On Days 3 to 7, inclusive, a daily dosage of about 0.02 mg to about 0.04 mg of ethinyl estradiol is administered. From Day 8 to Day 14, inclusive, a daily dosage of 0.035 mg ethinyl estradiol together with 0.5 mg norethindrone is administered. From Day 15 to Day 21, inclusive, 0.035 mg of ethinyl estradiol together with 0.75 mg norethindrone is administered daily. Following this, a third phase is begun where from Day 22 to Day 28, inclusive, a daily dosage of 0.035 mg ethinyl estradiol together with 1.0 mg of norethindrone is administered. This regimen is illustrated in TABLE III.

TABLE III

Contraceptive Regimen

| | | | | | | | |
|---|---|---|---|---|---|---|---|
| Day | 1 | 2 | 3 | 4 | 5 | 6 | 7 |
| Composition | P | P | E | E | E | E | E |
| Day | 8 | 9 | 10 | 11 | 12 | 13 | 14 |
| Composition | C1 | C1 | C1 | C1 | C1 | C1 | C1 |
| Day | 15 | 16 | 17 | 18 | 19 | 20 | 21 |
| Composition | C2 | C2 | C2 | C2 | C2 | C2 | C2 |
| Day | 22 | 23 | 24 | 25 | 26 | 27 | 28 |
| Composition | C3 | C3 | C3 | C3 | C3 | C3 | C3 |

Day = Day of the Menstrual Cycle: Day 1 is the first day of bleeding.
Composition = the active ingredient(s) present in a daily dosage unit taken on the respective day of the menstrual cycle.
P = placebo, contains no contraceptively active ingredients.
E = about 0.02 to about 0.04 mg ethenyl estradiol.
C1 = 0.035 mg ethinyl estradiol and 0.5 mg norethindrone.
C2 = 0.035 mg ethinyl estradiol and 0.75 mg norethindrone.
C3 = 0.035 mg ethinyl estradiol and 1.0 mg norethindrone.

The foregoing specification, including the specific embodiment and examples, is intended to be illustrative of the present invention and is not to be takes as limiting. Numerous other variations and modifications can be effective without departing from true spirit and scope of the present invention.

I claim:

1. A method of contraception *by suppressing recruitment of the dominant follicle* comprising:

(a) administering *orally* to a human female of child-bearing age, daily from [about Day 2 to about] *Day 3 or Day 4 through* Day 7 of her menstrual cycle, wherein Day 1 is the first day of menses, a first composition containing as sole contraceptively active ingredient an estrogenic compound at a daily dosage equivalent in estrogenic activity in the range of about 0.01 to about 0.04 milligrams of 17-alpha-ethinyl estradiol; and thereafter (b) administering *orally* to said female, daily through Day 28 of her menstrual cycle, at least one follow-up composition containing a contraceptively effective daily dosage of a progestin.

2. The method of contraception according to claim 1, wherein said follow-up composition contains a progestin as sole contraceptively active ingredient.

3. The method of contraception according to claim 1, wherein said follow-up composition comprises contraceptively effective amounts of an estrogenic compound and a progestin.

4. The method of contraception according to claim 1 wherein said estrogenic compound is ethinyl estradiol.

5. The method of contraception according to claim 1 wherein said estrogenic compound is mestranol.

6. The method of contraception according to claim 1 wherein said estrogenic compound is 17-beta-estradiol.

7. The method of contraception according to claim 1 wherein said follow-up composition contains norethindrone at a daily dosage in the range of about 0.5 mg to about 1.0 mg.

8. The method of contraception according to claim 1, wherein said progestin is D-norgestrel.

9. The method of contraception according to claim 1, wherein said progestin is D-17-beta-acetoxy-13-beta-ethyl-17-alpha-ethinyl-gon-4-en-3-one oxime.

10. The method of contraception according to claim 1, wherein said progestin is a 19-nor-17-hydroxy progesterone ester.

11. The method of contraception according to claim 1 wherein said estrogenic compound is ethinyl estradiol and said progestin is norethindrone.

12. The method of contraception according to claim 1 wherein said estrogenic compound is mestranol and said progestin is D-norgestrel.

13. The method of contraception according to claim 1 wherein plural follow-up compositions are administered in sequence, wherein the daily dosage of the estrogenic compound is substantially the same in all administered follow-up compositions, and wherein the daily dosage of progestin is greater in each successive follow-up composition.

14. The method of contraception according to claim 13 wherein said estrogenic compound is ethinyl estradiol and said progestin is norethindrone.

15. The method of contraception according to claim 14 wherein said daily dosage of ethinyl estradiol is about 0.035 mg.

16. The method of contraception according to claim 1 wherein plural follow-up compositions are administered in sequence, wherein the daily dosage of the estrogenic compound is substantially the same in all administered follow-up compositions; and wherein the daily dosage or progestin in successive follow-up compositions first increases to a value greater than the daily progestin dosage first administered and then decreases to the same value as the daily progestin dosage first administered.

17. The method of contraception according to claim 16 wherein said daily dosage of ethinyl estradiol is 0.035 mg.

18. A drug delivery system constituted by at least 24 separate daily dosage units, adapted for oral administration and comprising:

at least four *but not more than five* initial dosage units each containing as the sole contraceptively active ingredient the same contraceptively effective daily dosage of an estrogenic compound;

followed by twenty-one follow-up dosage units each containing a contraceptively effective daily dosage of a progestin.

19. The drug delivery system according to claim 18, wherein aid twenty-one follow-up dosage units each contain substantially the same daily dosage of a progestin.

20. The drug delivery system according to claim 18, wherein said twenty-one follow-up dosage units each contain substantially the same daily dosage of an estrogenic compound and a progestin.

21. The drug delivery system according to claim 18 wherein said twenty-one follow-up dosage units comprise a first group of 10 dosage units that each contain a first contraceptively effective daily dosage of an estrogenic compound and a progestin, and a second group of 11 dosage units that each contain a follow-up contraceptively effective daily dosage of a progestin and an estrogenic compound.

22. The drug delivery system according to claim 18 wherein said follow-up dosage units comprise three consecutive groups of about seven dosage units each, and wherein each of said groups individually comprises contraceptively effective daily dosage units of an estrogenic compound and a progestin present in substantially the same weight ratio, with the proviso that the weight ratios of said estrogenic compound to said progestin are different for the respective dosage units that constitute consecutively administered groups.

23. The drug delivery system according to claim 22 wherein the weight ratio of said estrogenic compound to said progestin is substantially the same in the first and the third consecutive groups of dosage units.

24. The drug delivery system according to claim 18 wherein said estrogenic compound present in said initial dosage units is ethinyl estradiol.

25. The group delivery system according to claim 18 wherein said estrogenic compound present in said initial dosage units is mestranol.

26. The drug delivery system according to claim 18 wherein said estrogenic compound present in said initial dosage units is 17-beta-estradiol.

27. The drug delivery system according to claim 18, wherein said progestin is norethindrone.

28. The drug delivery system according to claim 18 wherein said progestin is D-norgestrel.

* * * * *

UNITED STATES PATENT AND TRADEMARK OFFICE

CERTIFICATE OF CORRECTION

PATENT NO. : RE 35,724

DATED : February 3, 1998

INVENTOR(S) : Samuel A. Pasquale

It is certified that error appears in the above-identified patent and that said Letters Patent is hereby corrected as shown below:

Col. 7, line 37, claim 1: delete the phrase "by suppressing recruitment of the dominant follicle"

Signed and Sealed this

Thirtieth Day of March, 1999

*Attest:*

Q. TODD DICKINSON

*Attesting Officer*

*Acting Commissioner of Patents and Trademarks*